(12) United States Patent
Brinkley

(10) Patent No.: US 6,428,975 B1
(45) Date of Patent: Aug. 6, 2002

(54) METHODS FOR DETERMINING THE PRESENCE OR ABSENCE OF MICROORGANISMS IN LIPID-CONTAINING COMPOSITIONS

(75) Inventor: Michael A. Brinkley, Fuquay-Varina, NC (US)

(73) Assignee: Blue Ridge Pharmaceuticals, Inc., Greensboro, NC (US)

(*) Notice: Subject to any disclaimer, the term of this patent is extended or adjusted under 35 U.S.C. 154(b) by 0 days.

(21) Appl. No.: 09/483,228

(22) Filed: Jan. 14, 2000

(51) Int. Cl.[7] .............. C12Q 1/04; C12Q 1/00; C12M 1/00
(52) U.S. Cl. .......... 435/34; 435/4; 435/283.1; 435/243; 435/973; 435/842; 435/832
(58) Field of Search .......... 435/34, 4, 283.1, 435/243, 973, 842, 832

(56) References Cited

U.S. PATENT DOCUMENTS

| | | | |
|---|---|---|---|
| 5,372,943 A | * 12/1994 | Inlow et al. | 435/240.31 |
| 5,811,257 A | 9/1998 | Grant | 435/30 |
| 5,965,156 A | 10/1999 | Proffitt et al. | 424/450 |

FOREIGN PATENT DOCUMENTS

| | | | | |
|---|---|---|---|---|
| EP | 0 511 110 A2 | 4/1992 | | C12N/1/00 |
| JP | 05262657 A | * 1/1992 | | |
| WO | WO 96/01634 | 7/1995 | | A61K/31/65 |
| WO | 2001051650 | * 7/2001 | | |

OTHER PUBLICATIONS

Hjelmeland, "Solubilization of Native Membrane Proteins," Methods in Enzymology, vol. 182, pp. 253–264, 1990.

Löbenberg et al., "Modern Bioavailability, Bioequivalence and Biopharmaceutics Classification System. New Scientific Approaches to International Regulatory Standards," European Journal of Pharmaceutics and Biopharmaceutics, vol. 50, pp. 3–12, 2000.

* cited by examiner

Primary Examiner—Louise N. Leary
(74) Attorney, Agent, or Firm—Foley & Lardner

(57) ABSTRACT

The present invention provides methods of validating the sterility of compositions which contain large quantities of lipids, and especially those lipid compounds which contain quantities of bacteriocidal agents such as antibiotics. The compositions may contain quantities of phospholipids in the form of liposomes, microcrystals, or microdroplets. The methods involve dissolving the lipid composition in a diluent solution, passing the solution through a filtration device, and then incubating microbes which may be captured by the filtration device to determine whether microorganisms are present in the composition.

28 Claims, No Drawings

METHODS FOR DETERMINING THE PRESENCE OR ABSENCE OF MICROORGANISMS IN LIPID-CONTAINING COMPOSITIONS

The present invention relates to methods of detecting the presence or absence of microorganisms in and of validating the sterility of compositions which contain substantial quantities of lipids.

BACKGROUND OF THE INVENTION

Process validation refers to the concept of demonstrating the efficacy of a particular process through scientific methods. Injectable compositions which are to be administered to humans must be validated for sterility before the product can be safely released to consumers. This is commonly achieved through the use of a standard battery of microbiological tests which are based on the principle of attempting to isolate viable microorganisms from samples of the pharmaceutical product. Generally, this may involve passing the pharmaceutical product through a filter and isolating any microbes which may be present in the composition on the surface of the filter. The filter is then incubated in a microbiological medium and examined for microbial growth. Alternatively, the sample may be assayed for microbial growth by direct inoculation in a growth medium. By performing such assays with controls, scientists are able to demonstrate when the product of interest is free of contaminating microorganisms and therefore safe for distribution to consumers.

The validation of the sterility of lipid-rich compositions has presented particularly intractable problems. These compositions may include microcrystals, liposomes, microdroplets, and other compositions with a high lipid content. These compositions are generally unfilterable because their heavy lipid matrix quickly blocks the pores of the filter or membrane, thereby stopping the flow of liquid. Even the use of heat, emulsifiers, and pH adjustment often fail to convert these compositions into filterable solutions. While such products can sometimes be validated by direct inoculation, this is not feasible when the pharmaceutical or chemical product is itself bactericidal in nature. These problems are particularly acute, and these methods even more unsuitable, in circumstances where the product contains large quantities of antibiotics. Because of these obstacles, it has been thought that compositions which contain microcrystals., liposomes, and microdroplets are unfilterable. Presently, there are no available methods for filtering these compounds and validating their sterility such that they can be confidently distributed to consumers. This problem is particularly acute when the composition contains a bacteriocidal agent. We have observed the surprising result that these compounds can be brought to a filterable state by applying the chemical principles and schemes described herein.

The present invention provides a convenient, easily performed, and reliable method for determining the presence or absence of microorganisms or for validating the sterility of lipid-containing compositions. The method can be economically performed using commonly available chemicals and laboratory equipment within short timeframes to validate the sterility of products of interest. The methods disclosed herein are also suitable for validating the sterility of chemical and pharmaceutical products which contain large quantities-of antibiotics or other bacteriocidal agents.

SUMMARY OF THE INVENTION

The present invention provides methods of determining the presence or absence of microbes in a composition containing a lipid. In preferred embodiments, the lipid may be present in the composition in the form of a phospholipid, for example, as lecithin. In particularly preferred embodiments, the lipid may be present in the composition in the form of liposomes, microcrystals, or microdroplets. The composition may also contain a bacteriocidal agent, such as an antibiotic. In preferred embodiments, the bacteriocidal agent may be oxytetracycline, and the microbes may be a type of bacteria.

The method is conducted generally by dissolving the composition containing a lipid-in a diluent solution to form a diluted sample, passing the diluted sample through a filtration device, incubating the microbes which may be present on the filtration device for a time necessary to observe the growth of microbes which may be present, and examining the assay result to determine the presence or absence of microbes. The dissolution step may be accomplished by providing a diluent solution at a pH where the solubility of the composition containing the lipid, or the solubility of a major component of the composition, is enhanced relative to other pH points. In preferred embodiments, the diluent solution may comprise one or more solubilizers, and may also comprise a salt. The solubilizer may be an emulsifier, or a polysorbate (such as polysorbate 20) or sodium lauryl sulfate and the salt may be any water soluble metal/halogen salt. In particularly preferred embodiments, the salt is sodium chloride or potassium chloride.

The composition containing a lipid may be contacted with the diluent solution, such as by pouring or placing the composition into a bottle containing the diluent solution, or vice versa. The composition may be dissolved in the diluent solution, and then passed through a filtration device. The filtration device may be an ordinary nylon filter with pores of 0.2 $\mu$m or small enough to retain at least-a portion of the microbes being sought to be determined. The microbes which may be present on the filter may then be incubated for a period of time necessary to observe their growth. For example, the whole filter may be placed in an appropriate culture medium, or the filtration device filled with medium, or the organisms may be removed from the filter and placed into the medium. After incubation of the microbes, the assay result may then be read to determine if organisms were present in the sample.

The present invention therefore provides methods of validating the sterility of compositions containing lipids.

In preferred embodiments, the present invention may be employed for determining the presence or absence of microorganisms in compositions comprising antibiotics suspended in a phospholipid matrix. In preferred embodiments, the antibiotic may be oxytetracycline, the diluent solution may be a base, and the phospholipids may be present in the form of microcrystals, liposomes, or microdroplets. The diluent solution may also contain a salt and an emulsifier.

DETAILED DESCRIPTION OF THE INVENTION

Liposomes are multilamaellar vesicles. They generally have a lipid bilayer structure which is also layered within the total vesicle structure. Many layers may exist within the liposome.

Microdroplets comprise liquids encased in a layer of lipids. The lipid structure which surrounds and is part of the microdroplet is generally not multi-layered, but is generally a monolayer structure. Microdroplets typically have a diameter of from about 10 $\mu$m to about 40 or 50 $\mu$m.

Microcrystals are small crystals which usually have a lipid layer (but not a bilayer). They comprise a solid crystal encased in some type of lipid matrix. Microcrystals generally have a diameter of from about 0.5 μm to about 10 or even 20 μm.

By "bacteriocidal agent" is meant any composition which has the effect of inhibiting the growth of or destroying bacteria. Bacteriocidal agents may be antibiotics, detergents, or other chemicals (e.g., sodium azide) which inhibit the growth of or destroy bacteria.

By "solubilizer" is meant a compound which increases the solubility of another compound or composition.

The methods of the present invention may be broadly applied to lipid-containing compositions. The methods of the present invention may find particular utility for validating the sterility of compositions which are especially high in lipid content such as compositions containing liposomes, microdroplets, or microcrystals. These methods may find particular suitability in the determination of the presence or absence of microorganisms in or for the sterility validation of lipid-containing compounds which also contain highly insoluble antibiotics, for example, microcrystals which contain oxytetracycline. These compositions are provided as examples and are not intended to be limiting. The person of ordinary skill will realize that these principles are broadly applicable for determining the presence or absence of microorganisms or for validating the sterility of a wide variety of lipid-containing compounds. Compositions containing liposomes, microdroplets, and microcrystals have been very difficult or impossible to filter through a membrane with pores small enough to retain microbes which may be present in filtered solution, due to the high lipid content of these compositions. In particular, microcrystals may contain highly insoluble particulate materials which are coated with lipid. The lipid content of these compositions tends to quickly clog the pores of the membrane and stop the flow of liquid through the membrane. When high concentrations of antibiotics or other bacteriocidal compounds are encapsulated in these compositions, they destroy bacteria which may be "spiked" into samples for the purposes-of sterility validation controls, thereby negating the validity of the assay.

The principles of the present invention involve contacting the sample to be tested with a diluent solution which will at least partially solubilize the composition. The diluent solution may contain components-or be designed to have physico-chemical characteristics which are directed towards increasing the solubility of one or more components of the sample to be tested. The diluent solution may thus be an acidic or a basic solution, depending on the solubility or other chemical characteristics of the sample compound of interest at particular pH ranges. In a preferred embodiment, a detergent or emulsifier may be included to facilitate the breaking up and solubilization of the lipid matrix, thereby producing a composition in a sufficiently fluid state that it may be passed through a filter, membrane, or other type of filtration device with pores small enough to retain microbes which may be present in the solution. In a preferred embodiment, a combination of detergents and emulsifiers may be used at a concentration of from 1 to 10% w/v. For example, sodium lauryl sulfate (sodium dodecyl sulfate) or other similar emulsifiers of between 4 and 12 carbons in chain length may produce desirable results. Alternatively, polysorbates of between 20 and 80 carbons in chain length may produce desirable results. Microbes which may be captured on the filtration device may then be incubated with a broad spectrum growth medium which may be capable of supporting the growth of any microbes which may be present. In a preferred embodiment, the medium may be capable of supporting reproductive growth of microbes. In particularly preferred embodiments, the medium may be trypticase soy broth (USP), or fluid thioglycolate medium (USP) or another suitable microbe growth medium.

The methods may also be applied to facilitate the handling of lipid-containing compositions for a variety of other purposes as well. For example, the present invention-may be applied to enhancing analytical assays for which it would be useful to solubilize the lipid content of a sample to be tested. The invention may also be useful in assays where it would be advantageous to increase the reactivity of an analyte within a lipid matrix with a chromophore. The present methods may also be applied for enhanced waste disposal, or enhanced spill clean up in which it may be advantageous to solubilize a lipid matrix prior to disposal. The person of ordinary skill will realize that the present invention is also applicable to other applications where solubilization of a lipid rich material is desirable, and that these applications are meant to be within the scope of the present invention.

The methods of the present invention may be applicable to a wide variety of lipid containing compositions with only minor adjustments to the method.

Generally, the methods of the present invention involve consideration of the solubility profile of the particular composition in question. The pH of the composition should be adjusted with consideration to that profile and the composition adjusted to a pH where its solubility or the solubility of a major component of the composition is enhanced relative to other pH values. Solubilizers, such as detergents, emulsifiers, or other solubilizing agents may then be added in appropriate quantities to solubilize the lipid matrix, the compound of interest, or another major component of the composition. Sodium chloride, potassium chloride, or another water soluble metal/halogen salt may also be added since it has been found to further solubilize lipid matrices, such as lecithin. The surprising result of applying the above concepts may be a diluent solution which is capable of solubilizing the composition of interest, and rendering it filterable. The diluted and solubilized composition may then be filtered and the microbes captured on the filter, membrane, or other filtration device incubated and examined for signs of microbial growth in conventional fashion.

The methods are further illustrated through the following examples. These examples are provided only as representative examples and are not intended to be limiting. The person of ordinary skill will realize that these methods may be applied to determination of-the presence or absence of bacteria, or to facilitate the sterility validation of a variety of compounds.

EXAMPLE 1

This example illustrates how the methods of the present invention were applied to validate the sterility of 25% oxytetracycline dihydrate suspended in a phospholipid syrup (lecithin) matrix. The unmodified product was not filterable since its phospholipid matrix quickly clogged the pores of a 0.45 μm membrane. This type of composition presents particularly difficult problems with validation assays because the oxytetracycline is itself an antibiotic. Therefore, sterility validation by direct injection of the compound into a growth medium was not feasible. In addition to oxytetracycline (25% w/v) suspended in a phospholipid syrup (20% w/v), the formulation also contained mannitol (2.25% w/v), methylparaben (0.18% w/v), propylparaben (0.02% w/v), sodium hydroxide, hydrochloric acid, and water for injection. The nominal pH of the product was 6.50. The solubility profile for oxytetracycline dihydrate indicated it was most soluble at pH 9.0. It was also discovered that lecithin is soluble in NaCl. Therefore, a diluent solution was prepared which contained the following:

970 ml deionized water 30 ml polysorbate 20

20 g sodium lauryl sulfate 15 g Tris base (Tris(hydroxymethyl)aminomethane)

optionally, 10 g of sodium chloride

The solution was pH adjusted to 8.75±0.02 with HCl and placed into 1 L size glass bottles with screw tops and septums. This diluent solution was then sterilized by autoclaving.

Following sterilization of the diluent solutions, a control bottle was chosen randomly. This bottle was used only to determine pH adjustments or titrations and was not used for testing. Using a 60 ml syringe and large gauge needle (16G), 50 ml of oxytetracycline suspension was aseptically removed through the product-container's septum and added to the control bottle. The control bottle was shaken well and a portion was removed to determine the pH. The pH was adjusted to 8.65–8.75 using 10 N NaOH, added dropwise. The amount of NaOH added was recorded.

Two bottles of diluent solution were heated to 40° C. in a water bath. 50 ml of the oxytetracycline suspension sample was removed and added to each sterilized diluent solution in the same aseptic manner as the control bottle. NaOH was added in an amount equal to that determined with the control bottle. The contents of the two bottles were then passed through STERITEST® (Millipore Corp., Mass.) filters, although equivalent microbiological filters which are commonly available may, of course, also be used in the method. For example, 0.2 μm nylon filters may be useful in practicing the present invention. Each filter was rinsed with 500 ml of Fluid A upon completion of the filtering of the one liter of diluent solution sample. After the rinsing, 100 ml of tryptic soy broth (TSB) was added to one filter canister and 100 ml of fluid thioglycolate medium (FTM) was added to the other. The TSB bottle was then incubated for 14 days at 20–25° C. and FTM bottle was incubated for 14 days at 30–35° C. Test articles were considered sterile if they were free of turbidity at the end of the 14 days.

Fluid A (also known as diluting fluid A, rinsing fluid A, and dilute peptic digest) was comprised of 1.0 g of peptic digest of animal tissue (bacteriological peptone) and 1000 mL of deionized water.

Tryptic soy broth (TSB, also known as-trypticase soy broth or soybean-casein digest medium) was comprised of the following:

| Pancreatic digest of casein | 17.0 g |
|---|---|
| Papaic digest of soybean meal | 3.0 g |
| Sodium chloride | 5.0 g |
| Dibasic potassium phosphate | 2.5 g |
| Dextrose | 2.5 g |
| purified Water (deionized) | 1000 mL |

Fluid Thioglycolate Medium (FTM) was comprised of the following:

| L-Cystine | 0.5 g |
|---|---|
| Sodium chloride | 2.5 g |
| Dextrose | 5.5 g |
| Agar, granulated | 0.75 g |
| Yeast extract (water soluble) | 5.0 g |
| Pancreatic digest of casein | 15.0 g |
| Sodium thioglycolate or thioglycolic acid | 0.5 g |
| Resazurin sodium solution (1 in 1000, freshly prepared) | 0.3 ml |
| purified water (deionized) | 1000 ml |

EXAMPLE 2

This example illustrates how the method itself was validated. Due to the nature of the sample manipulations, not only were test organisms placed in the final rinse with Fluid A, but were also spiked into sterilized diluent bottles prior to the pH adjustment and diluent solution was then treated as a test article (without addition of oxytetracycline product). Test organisms were also spiked into Fluid A and filtered through to serve as a positive control.

Following the pH determination/titration of the control bottle, 50 ml of the oxytetracycline suspension was added to 1 L of the sterilized diluent solution. The pH of the solution was 7.95. 10 N NaOH was added dropwise to the bottle (six drops) to achieve a final pH of 8.65.

Five bottles of sterility diluent solution were heated to 40° C. for testing of spiked diluent solution. Each bottle containing sterility diluent solution was spiked with 10–100 cfu of test organisms. The five bottles were dedicated as follows: TSB and *Candida albicans*, FTM and *Candida albicans*, TSB and *Bacillus subtilis*, FTM and *Bacillus subtilis*, FTM and *Clostridium sporogenes*. The pH was adjusted to 7.95 with HCl, then 6 ml of NaOH was added to simulate product handling.

Two bottles of sterility diluent were heated to 40° C. for product testing. Two other bottles of sterility diluent were heated to 40° C. for the sterility check of the diluent.

A bottle of sterility diluent containing 10–100 cfu of *Candida albicans* was filtered through a single side of a dual canister STERITEST® unit. 500 ml of Fluid A was used to rinse the filter and 100 ml of FTM was then added to the canister. The process was repeated for *Candida albicans* using TSB media, and *Bacillus subtilis* using TSB and FTM, and *Clostridium sporogenes* using FTM.

For the positive control, 0.1 ml of *Clostridium sporogenes* was added directly to the final 100 ml of the 500 ml Fluid A rinse and 100 ml of FTM was added to the STERITEST® canister. The process was repeated for *Candida albicans* using FTM and TSB and *Bacillus subtilis* using FTM and TSB.

For the product test two 50 ml portions of the oxytetracycline suspension in two 1 L sterility diluent bottles were filtered through STERITEST® canisters. Each membrane was rinsed with 500 ml of Fluid A. After rinsing, one canister was filled with 100 ml of FTM and the other with 100 ml of TSB.

For sterility testing of the sterility diluent solution, two 1 L size bottles of sterility diluent solution were filtered through STERITEST® canisters. Each membrane was rinsed with 500 ml of Fluid A. After rinsing one canister was filled with 100 ml of FTM and the other with 100 ml of TSB.

For negative control, 500 ml of Fluid A was rinsed through a STERITEST® canister for each membrane. After rinsing, one canister was filled with 100 ml of FTM and the other with 100 ml of TSB.

All FTM STERITEST® canisters were incubated at 30–35° C. for 14 days and all TSB canisters were incubated at 20–25° C. for 14 days. Canisters were examined periodically and at the end of the 14 days for signs of turbidity. The positive controls, positive diluent spikes, and positive product spikes all showed signs of microbial growth (turbidity). The onset of the turbidity and the level of turbidity were equivalent in all samples tested. All negative control, diluent tests, and product tests showed no signs of turbidity after 14 days.

What is claimed is:

1. A method of determining the presence or absence of microbes in a composition containing a lipid, comprising:
    dissolving the composition containing a lipid in a diluent solution to form a diluted sample, the dissolving of the composition being performed by;
        providing the diluent solution at a pH where the solubility of the composition containing a lipid or the solubility of a major component of the composition containing a lipid is enhanced relative to the solubility at other pH points, the diluent solution comprising one or more solubilizers; and
        contacting the composition containing a lipid with the diluent solution;
    passing the diluted sample through a filtration device;
    incubating the microbes which may be present on the filtration device for a time necessary to observe the growth of microbes which may be present; and
    examining the assay result to determine the presence or absence of microbes.

2. The method of claim 1 wherein the diluent solution further comprises a salt.

3. The method of claim 1, wherein the composition containing a lipid contains liposomes, microdroplets, or microcrystals.

4. The method of claim 1, wherein the composition containing a lipid contains a phospholipid.

5. The method of claim 4, wherein the phospholipid is a lecithin.

6. The method of claim 4 wherein the phospholipid is comprised in microcrystals, liposomes, or microdroplets.

7. The method of claim 1 wherein the composition containing a lipid further comprises a bacteriocidal agent.

8. The method of claim 7 wherein the bacteriocidal agent is an antibiotic.

9. The method of claim 8 wherein the antibiotic comprises oxytetracycline.

10. The method of claim 1 wherein the solubilizer comprises an emulsifier.

11. The method of claim 1 wherein the solubilizer is an emulsifier of between four and eleven carbons.

12. The method of claim 1 wherein the solubilizer is a polysorbate and/or sodium lauryl sulfate.

13. The method of claim 12 wherein the polysorbate is polysorbate 20.

14. The method of claim 1 further comprising a water soluble metal/halide salt.

15. The method of claim 14 wherein the salt is sodium chloride or potassium chloride.

16. The method of claim 1 wherein the one or more solubilizers comprise polysorbate 20 and/or sodium lauryl sulfate, and further comprising a water soluble metal/halogen salt.

17. A method of determining the presence or absence of microbes in a composition comprising an antibiotic suspended in a phospholipid matrix, comprising:
    dissolving the composition in a diluent solution to form a diluted sample, the dissolution being performed by;
        providing the diluent solution at a pH where the solubility of the composition or the solubility of a major component of the composition is enhanced relative to the solubility at other pH points, the diluent solution comprising one or more solubilizers and a salt;
        contacting the composition with the diluent solution;
    passing the diluted sample through a filtration device;
    incubating the microbes which may be present on the filtration device for a time necessary to observe the growth of microbes which may be present;
    examining the assay result to determine the presence or absence of microbes.

18. The method of claim 17, wherein the composition containing a lipid contains liposomes, microdroplets, or microcrystals.

19. The method of claim 17, wherein the composition containing a lipid contains a phospholipid.

20. The method of claim 19, wherein the phospholipid is a lecithin.

21. The method of claim 19 wherein the phospholipid is comprised in microcrystals, liposomes, or microdroplets.

22. The method of claim 17 wherein the antibiotic comprises oxytetracycline.

23. The method of claim 17 wherein the solubilizer comprises an emulsifier.

24. The method of claim 17 wherein the solubilizer is a polysorbate or sodium lauryl sulfate.

25. The method of claim 17 wherein the solubilizer is an emulsifier of between 4 and 11 carbons.

26. The method of claim 24 wherein the polysorbate is polysorbate 20.

27. The method of claim 17 wherein the salt is a water soluble metal/halide salt.

28. The method of claim 27 wherein the water soluble metal/halide salt is sodium chloride or potassium chloride.

* * * * *